(12) United States Patent
Nayar

(10) Patent No.: US 12,167,833 B2
(45) Date of Patent: Dec. 17, 2024

(54) BIOPSY VALVE WITH ACCESSORY TOOL TACTILE GUARD CAP POSITION MARKER

(71) Applicant: EndoSpace Corporation, Newport, DE (US)

(72) Inventor: Devjit Nayar, Jersey City, NJ (US)

(73) Assignee: EndoSpace Corporation, Newport, DE (US)

(*) Notice: Subject to any disclaimer, the term of this patent is extended or adjusted under 35 U.S.C. 154(b) by 629 days.

(21) Appl. No.: 17/445,766

(22) Filed: Aug. 24, 2021

(65) Prior Publication Data

US 2022/0061639 A1 Mar. 3, 2022

Related U.S. Application Data

(60) Provisional application No. 63/072,359, filed on Aug. 31, 2020.

(51) Int. Cl.
*A61B 1/00* (2006.01)
*A61B 1/018* (2006.01)
*A61B 10/04* (2006.01)
*A61M 39/02* (2006.01)

(52) U.S. Cl.
CPC ........ *A61B 1/00137* (2013.01); *A61B 1/0011* (2013.01); *A61B 1/018* (2013.01); *A61B 10/04* (2013.01); *A61M 2039/0202* (2013.01)

(58) Field of Classification Search
CPC ..... A61B 1/00137; A61B 1/018; A61B 10/04; A61B 1/0011–00112; A61B 1/00131; A61B 1/0014; A61B 1/00121; A61B 1/012; A61M 2039/0202; A61M 25/0075
See application file for complete search history.

(56) References Cited

U.S. PATENT DOCUMENTS

| 7,967,744 | B2 | 6/2011 | Kaye et al. |
| 8,070,756 | B2 | 12/2011 | Secrest et al. |
| 2006/0235433 | A1* | 10/2006 | Secrest ............ A61B 17/32056 606/114 |
| 2010/0024956 | A1 | 2/2010 | Vogler |

(Continued)

FOREIGN PATENT DOCUMENTS

CN 111938831 A * 11/2020 ....... A61B 17/00234

OTHER PUBLICATIONS

English Translation of CN 111938831 A, Micro Tech Nanjing Co Ltd, 10 pages, printed on Mar. 20, 2024,. (Year: 2020).*

*Primary Examiner* — Matthew Kremer
*Assistant Examiner* — Jennifer Grace Baires-Tweed
(74) *Attorney, Agent, or Firm* — Harris Beach PLLC

(57) ABSTRACT

A biopsy valve includes a body having a first groove adapted to fit over a lip of an endoscope working channel and a second groove and a first membrane. A primary cap is mechanically coupled to the body by a primary strap extending between the primary cap and the body. The primary cap includes a primary cap lip to couple into the second groove of the body, a second membrane and a primary cap groove. A guard cap is mechanically coupled to the body by a guard cap strap extending between the guard cap and the body. The guard cap includes a guard cap lip which couples into the primary cap groove of the primary cap, and a third membrane. A triple membrane biopsy valve and a method of using a biopsy valve with an endoscope working channel are also described.

9 Claims, 19 Drawing Sheets

(56) References Cited

U.S. PATENT DOCUMENTS

| | | | |
|---|---|---|---|
| 2011/0276051 A1* | 11/2011 | Blakemore | A61B 17/1764 |
| | | | 606/87 |
| 2012/0071713 A1* | 3/2012 | Kaye | A61B 1/00137 |
| | | | 600/104 |
| 2013/0171030 A1* | 7/2013 | Ferlic | A61M 39/20 |
| | | | 422/294 |
| 2014/0187866 A1 | 7/2014 | Kaye et al. | |
| 2016/0106400 A1* | 4/2016 | Cho | A61B 10/04 |
| | | | 600/562 |
| 2016/0245729 A1* | 8/2016 | Yamakawa | B01L 3/021 |

\* cited by examiner

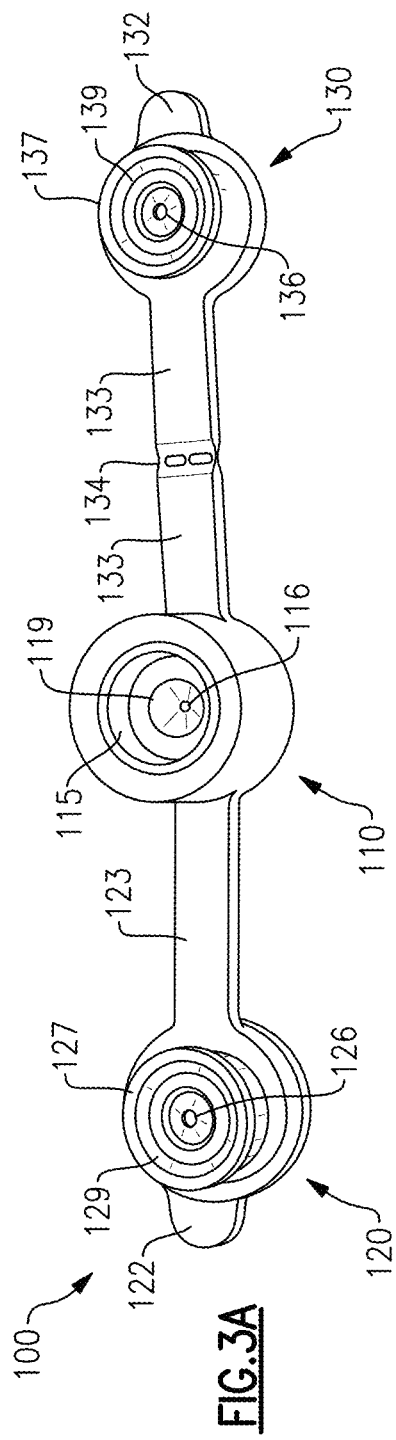
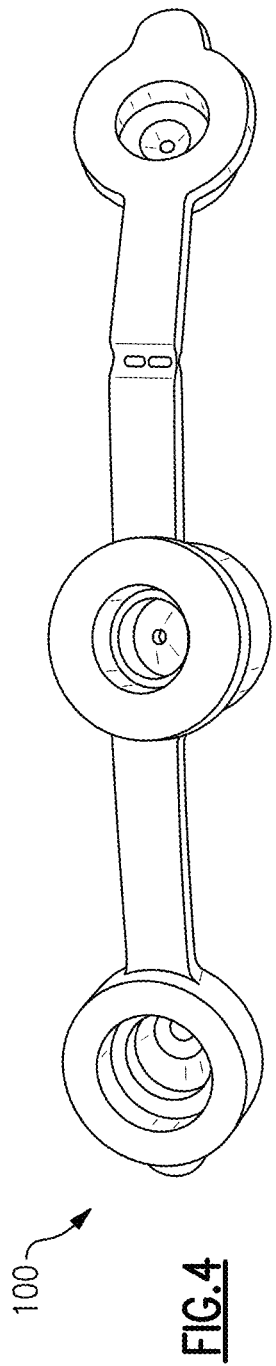

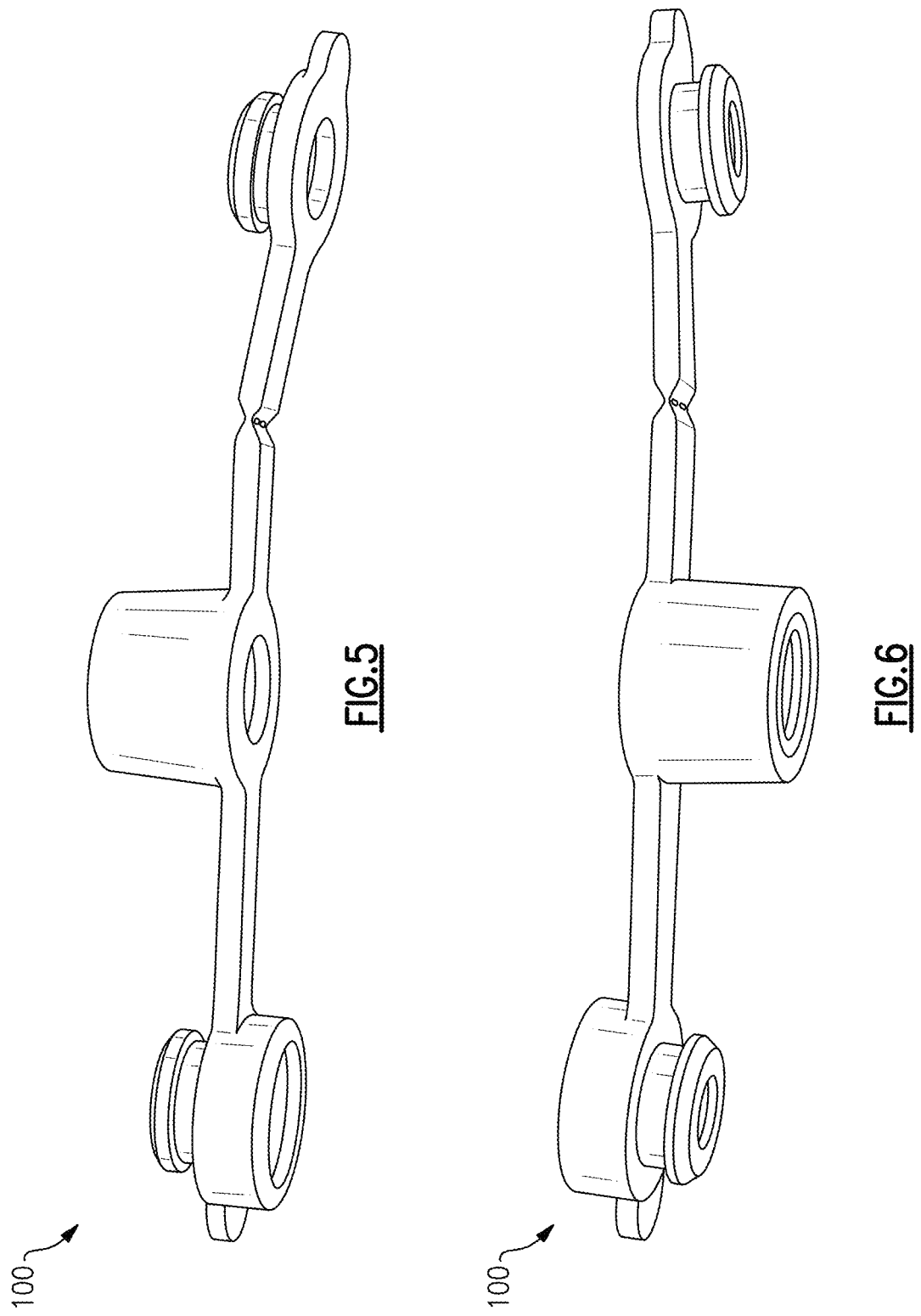

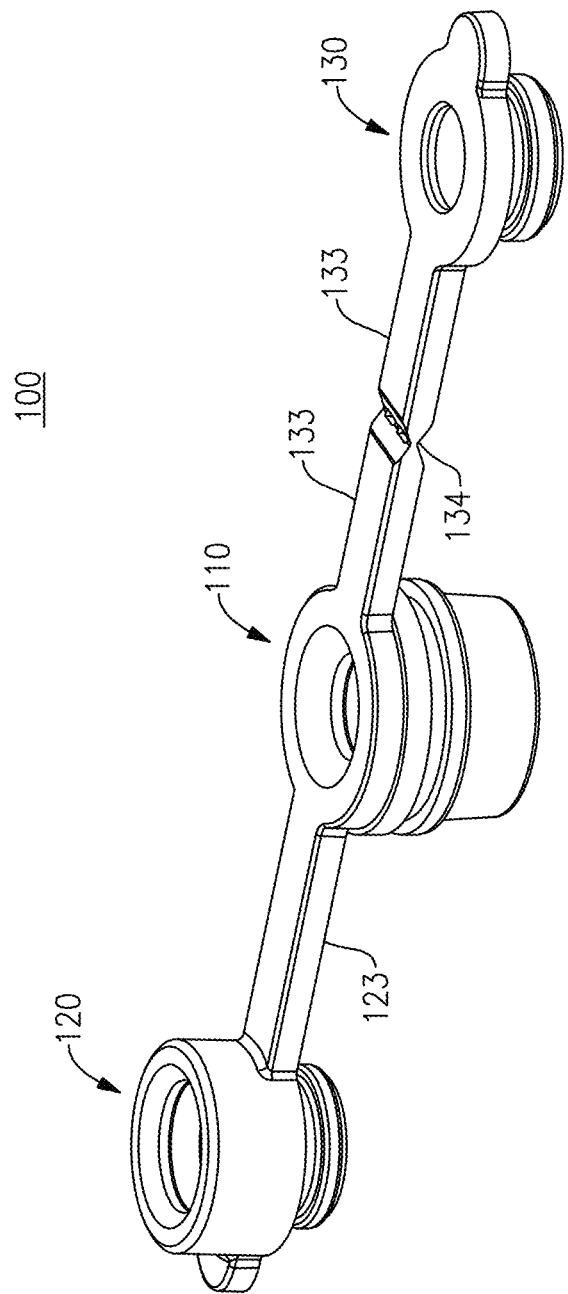

BIOPSY VALVE WITH ACCESSORY TOOL TACTILE GUARD CAP POSITION MARKER

CROSS-REFERENCE TO RELATED APPLICATIONS

This application claims priority to and the benefit of U.S. provisional patent application Ser. No. 63/072,359, BIOPSY VALVE WITH ACCESSORY TOOL TACTILE GUARD CAP POSITION MARKER, filed Aug. 31, 2020, which application is incorporated herein by reference in its entirety.

FIELD OF THE APPLICATION

The application relates to endoscopy, particularly to a biopsy valve fitted onto the working channel of an endoscope.

BACKGROUND

An endoscope allows a medical practitioner to place an insertion tube within a lumen of the human body. Common endoscopic procedures include esophagogastroduodenoscopy, colonoscopy, sigmoidoscopy, endoscopic retrograde cholangiopancreatography, and endoscopic ultrasound. Endoscopy allows for examination and biopsy of tissue of the esophagus and colon. Accessory tools, such as biopsy snares, forceps, needles, and clips can be inserted into a lumen of the human body via a working channel of the endoscope.

SUMMARY

A biopsy valve includes a body having a first groove adapted to fit over a lip of an endoscope working channel and a second groove and a first membrane. A primary cap is mechanically coupled to the body by a primary strap extending between the primary cap and the body. The primary cap includes a primary cap lip to couple into the second groove of the body, a second membrane and a primary cap groove. A guard cap is mechanically coupled to the body by a guard cap strap extending between the guard cap and the body. The guard cap includes a guard cap lip which couples into the primary cap groove of the primary cap, and a third membrane.

The guard cap strap can be longer in length than the primary strap. The guard cap strap can include a tear line. The guard cap can be severed along the tear line and is configured to friction fit to a shaft of an accessory tool which rides freely on the shaft of the accessory tool when removed from a working channel of an endoscope, and when the accessory tool is reinserted into the working channel, the guard cap touches a top of the primary cap providing a tactile feedback of the shaft of the accessory tool in an insertion tube of the endoscope. The guard cap strap can include a perforated tear line.

The biopsy valve can include a silicone material. The biopsy valve can be manufactured by a molding process.

A triple membrane biopsy valve includes a body having a first groove adapted to fit over a lip of an endoscope working channel and a second groove and a first membrane. A primary cap is mechanically coupled to the body by a primary strap extending between the primary cap and the body. The primary cap includes a primary cap lip which couples into the second groove of the body, a second membrane and a primary cap groove. A guard cap is mechanically coupled to the body by a guard cap strap extending between the guard cap and the body. The guard cap includes a guard cap lip which couples into the primary cap groove of the primary cap, and a third membrane. The primary cap is pushed into the second groove of the body and the guard cap pushed into the primary cap groove which provides a biopsy valve with a triple membrane.

A method of using a biopsy valve with an endoscope working channel includes: providing a triple membrane biopsy valve with a primary cap and a guard cap; installing a body of the triple membrane biopsy valve onto a working channel of the endoscope; folding over and plugging the primary cap into the body; folding over and plugging the guard cap into the primary cap; and inserting a shaft of an accessory tool through a third membrane of the guard cap, a second membrane of the primary cap, and a first membrane of the body.

After the step of inserting, there can be a further step of severing a guard cap strap between the body and the guard cap, and unplugging the guard cap from the primary cap as the shaft of the accessory tool is removed from the working channel, and on reinsertion of the shaft of the accessory tool into the working channel, detecting by a tactile feedback when the guard cap riding by a friction fit at a location on the shaft of the accessory tool, touches a top surface of the primary cap.

The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

FIG. 3A is a drawing showing a bottom view of an exemplary biopsy valve with accessory tool tactile guard cap position marker according to the Application;

FIG. 4 is a drawing showing a top view of the biopsy valve of FIG. 3;

FIG. 5 is a drawing showing a first side view of the biopsy valve of FIG. 3;

FIG. 6 is a drawing showing a second side view of the biopsy valve of FIG. 3;

FIG. 16A is a drawing showing an elevated view of ValveGuard similar to FIG. 4.

DETAILED DESCRIPTION

Figure 1:
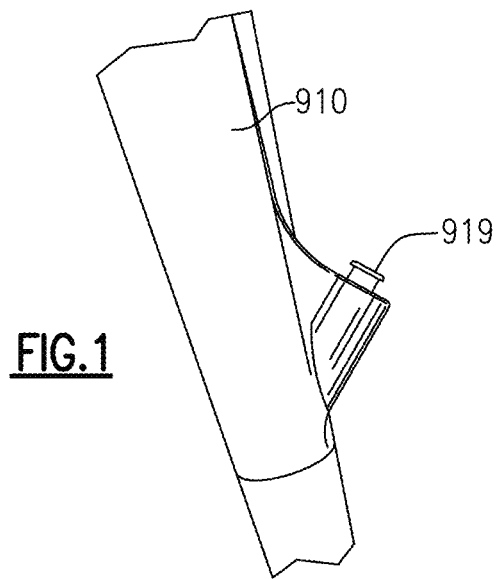
FIG. 1 is a drawing showing an exemplary standard endoscope.

A biopsy valve according to the Application adds new structure compared to a typical biopsy valve of the prior art. We refer to one exemplary biopsy valve with accessory tool tactile guard cap position marker according to the Application as ValveGuard.

Medical professionals that perform endoscopy have complained about bio fluid splatter, and an inability to obtain tactile feedback when an accessory is about to come into view within a lumen such as the intestinal lumen. Oftentimes, the medical practitioner relies only on visual clues. The risks with over-passage of accessories such as needles, clips, or biopsy forceps, include mucosal trauma, and possibly even perforation of a lumen wall. Endoscopy technicians have described multiple occasions where mucosa was traumatized from inadvertent over passage of accessories while using caps of the prior art. Such inadvertent perforation can include adjacent organ involvement.

In addition, medical centers use accessories supplied by third-party accessory manufactures whose manufacturing specifications are often slightly different than the dimensions of the accessories manufactured by the original equipment manufacturer. Consequently, the diameter of certain accessories manufactured by third party manufacturers can be slightly smaller than the OEM accessories, due to the manufacturing variances. With caps of the prior art, if there was any tactile feedback, it was as the distal end of an accessory exits the endoscope. However, such third party accessory dimension variances can limit the tactile feedback when the distal end of an accessory exits the endoscope, which the practitioner may have originally felt with larger dimensions of the OEM accessories.

It was realized that both problems of bio fluid splatter and over-passage, can be solved by an additional strap and cap structure. A biopsy valve according to the Application, such as ValveGuard, provides two caps on the biopsy valve to prevent via splatter. The secondary cap or guard cap of the biopsy valve of the Application can be friction fit onto any suitable accessory so that when the medical practitioner inserts the accessory, the secondary cap acts as a stopper. Further advancement of accessories into a lumen calls for slightly more manual force of advancement to overcome the friction fit of the secondary cap and the accessory, thereby giving clear tactile feedback to the medical practitioner, and preventing over passage of said accessory through the channel. In addition, the color schemes of certain endoscopic accessories in a dark room make it difficult to see visual cues or markings on the accessory. For both of these reasons, the new structure of the removable secondary (guard cap) according to the Application, when friction fitted onto any accessory from virtually any manufacturer, provides a new safety stop.

TABLE OF REFERENCE DESIGNATORS 100 biopsy valve
110 body
111 first groove (body)
115 second groove (body)
116 hole (body)
119 first membrane (body)
120 primary cap
122 tab (primary cap)
123 strap (primary cap)
125 primary cap groove (primary cap)
126 hole (primary cap)
127 lip (primary cap)
129 second membrane (primary cap)
130 guard cap
132 tap (guard cap)
133 strap (guard cap)
134 tear line (guard cap strap)
136 hole (guard cap)
137 lip (guard cap)
139 third membrane (guard cap)

FIG. 1 is a drawing showing an exemplary standard endoscope 910. The various controls and features of a standard endoscope allow a medical professional to steer the end of the insertion tube 909 through a portion of a lumen within a body of a patient, for example through an intestine. The insertion tube allows for accessories to be threaded within. The endoscope includes an optical view or a camera which allows the practitioner to view the parts of the body near the end of the insertion tool as it is advanced, for example, through the intestine. Accessory tools which can be inserted through a working channel and through the insertion tube of the endoscope, include biopsy tools which allow, for example, the practitioner to take one or more biopsy samples at one or more locations within the lumen of the body. A snare tool, a forceps tool, and/or any suitable accessory cutting mechanism can be used for such biopsy purposes to obtain biological samples.

Accessory tools are placed in the endoscope's insertion tube through working channel 919. Generally, endoscopes use a standard tongue and groove type connection, referred to hereinbelow as a lip and groove connector or connection. Viewed from the side, as shown in FIG. 1, the top of the working channel connection, the lip is the top of the "T" part. A corresponding groove is present on the part which affixes to the working channel, typically referred to in the art as a biopsy valve.

A typical biopsy valve includes a body which includes a groove which corresponds to and locks onto the lip at the apex of the working channel 919 connection. The body typically includes a first membrane, usually with a precut hole 116 or slot through which the shaft of the accessory is inserted through the biopsy valve and into the insertion tube 909 of the endoscope. Also, there is typically a primary cap which is attached to the body by a flexible strap or tether. The primary cap also includes a membrane, which similar to the body membrane has a precut hole 126 or slit. In use, the primary cap and strap are folded over and the primary cap is pressed into and couples to the body of the biopsy valve, generally by use of a similar or substantially the same lip and groove connection as used throughout. The only slight difference is where the lip of the working channel is typically a metal, the rest of the lip and groove coupling are of the same material as the biopsy valve, typically a plastic or silicone.

Here, the groove is in the top of the body (opposite the side of the body which snaps onto the working channel of the endoscope), and the lip is on the end of the primary cap. Once folded over, the strapped primary cap remains in place for the entirety of the medical procedure, following which, the onetime use biopsy valve is generally discarded as medical waste. In operation, there are two membranes, the membrane of the body, and the membrane of the primary cap. The installed and assembled double membrane prevents reflux bodily fluids from leaking out of the working port. During use, the practitioner may introduce air into the lumen of the body to slightly expand the lumen (e.g. a wall of the intestine) to make for a better view. Another function of the double membrane biopsy valve is to reduce the escape of air from the working port.

Figure 2:
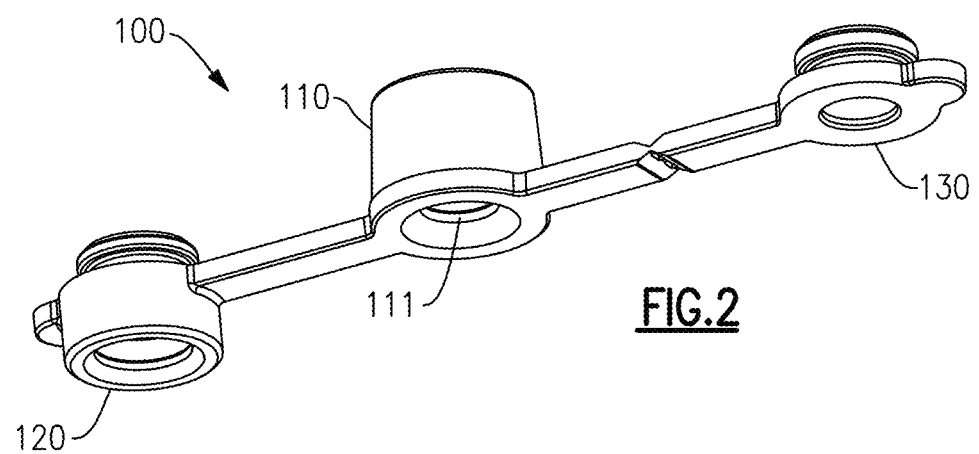
FIG. 2 is a drawing showing an improved biopsy valve according to the Application.

FIG. 2 is a drawing showing an improved biopsy valve according to the Application. Body 110 and primary cap 120 are similar to biopsy valves of the prior art. What is new is the guard cap 130. The guard cap 103 is mechanically coupled to the body 110 by a guard cap strap 133. Guard cap strap 133 is longer than the primary strap 123 which affixes the primary cap 120 to the body 110, so that the guard cap 130 and guard cap strap 133 can be folded over so that the guard cap can be coupled into the end of the primary cap by a similar lip and groove type connection. The guard cap 130 typically includes a precut hole 136 or slit to also allow for insertion of the accessory tool shaft through a third membrane of the guard cap.

The new guard cap 130 has two uses. In a first use, the guard cap provides a third membrane over the working channel to further protect against unwanted bodily fluids escaping the working channel as well as to further limit the loss of air intentionally injected by the practitioner to inflate the lumen for an improved view of the structure and physiology within. In some uses, the guard cap remains mechanically coupled by the lip and groove, to the primary cap for the entire endoscopic procedure. The tertiary membrane is effective for an improved seal with the working channel.

However, it is also common for the practitioner to repeatedly remove and insert the accessory tool, such as to remove the tissue of biopsied samples, which means the accessory tool is fully removed from the working channel and the biopsy valve. In such cases, the shaft of the accessory tool is completely removed from both membranes of the body and primary cap each time the tool is withdrawn. Then the shaft of the accessory tool is re-inserted into the same biopsy valve for successive tissue biopsy samples.

A problem is that on reinsertion, the practitioner must be mindful of both the location of the insertion tube of the endoscope, as well as the advancing position of the shaft of the accessory tool on re-insertion into the lumen of the patient being inspected and sampled. A danger is that the practitioner, while correctly positioning the insertion tube, can lose track of the advancing shaft of the accessory tool and scratch, tear, or even inadvertently puncture the lumen, causing injury to the patient.

Applicant realized that what is needed is an additional part to give a tactile feel for reinsertion. While the guard cap is typically coupled by the lip and groove connection into the top of the primary valve, it was realized that by uncoupling the guard cap and letting it ride back with the retreating shaft of the accessory tool, the guard cap can provide a positive marker which can indicate a location of the end of the shaft of the accessory tool near the end of the insertion tube of the endoscope. Because of the friction hold of the guard cap onto the outer surface of the shaft of the accessory tool, once uncoupled, the guard cap can ride back and away from the working port of the endoscope. Then, on reinsertion, such as for successive biopsy samples, the shaft of the accessory tool can be advanced back into the insertion tube of the endoscope, until the guard cap touches or taps the top of the primary cap, thus providing a positive tactile feel to the practitioner that the end of the shaft of the accessory tool is near or just through the end of the insertion tube of the endoscope. Thus, the danger of accidentally advancing the shaft of the accessory tool into the lumen of the patient is greatly reduced.

Strap 133 for this latter use as a shaft of the accessory tool position marker, in addition to being longer than strap 123, can have a perforated section, such as a perforated tear line. At the first extraction of the shaft of the accessory tool, the strap is severed, e.g. pulled apart, before the shaft of the accessory tool is pulled back. That way, once uncoupled, the guard cap rides back with the shaft of the accessory tool at substantially the same position (because the friction fit between the hole or slit of the membrane of the guard cap and the shaft of the accessory tool) to be used as a position marker, and tactile feedback, for the successive reinsertion of the shaft of the accessory tool into the insertion tube of the endoscope.

Figure 3B:
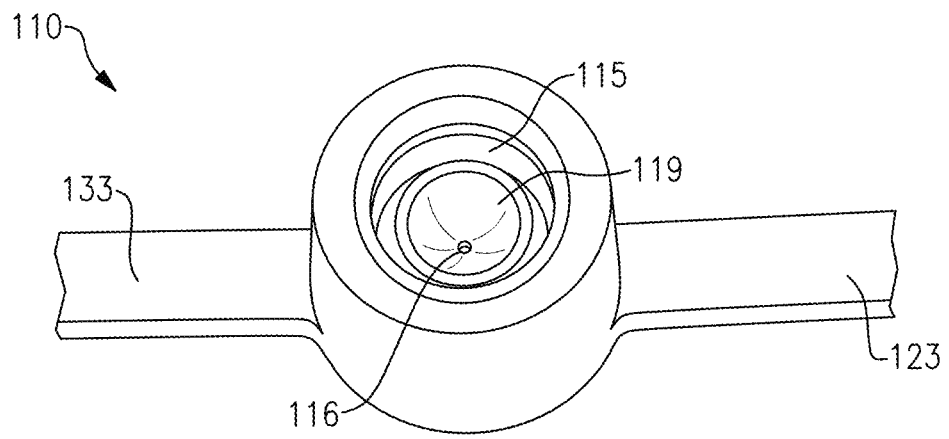
FIG. 3B is a drawing showing an elevated view of the primary cap side of the body of the exemplary biopsy valve of FIG. 3A.
Figure 3C:
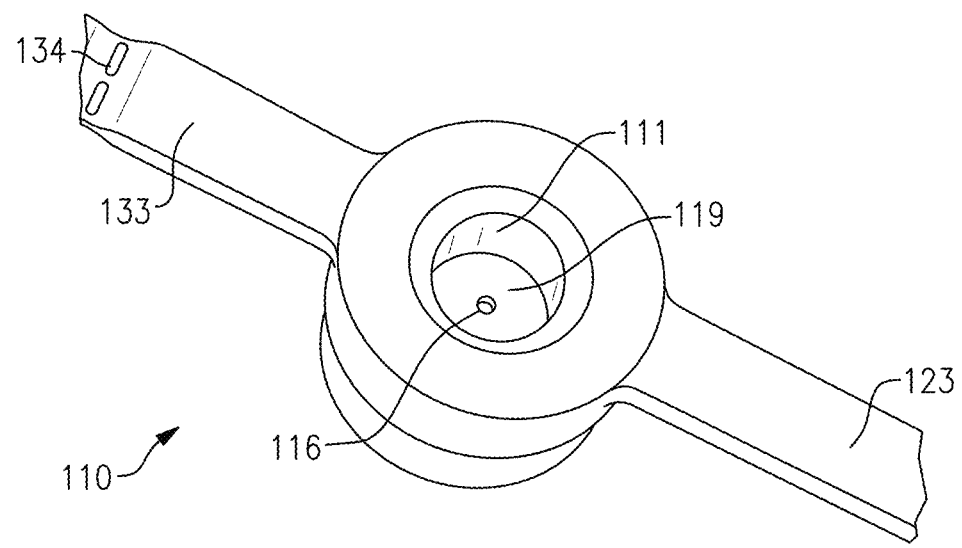
FIG. 3C is a drawing showing an elevated view of the endoscope working channel side of the body of the exemplary biopsy valve of FIG. 3A.
Figure 3D:
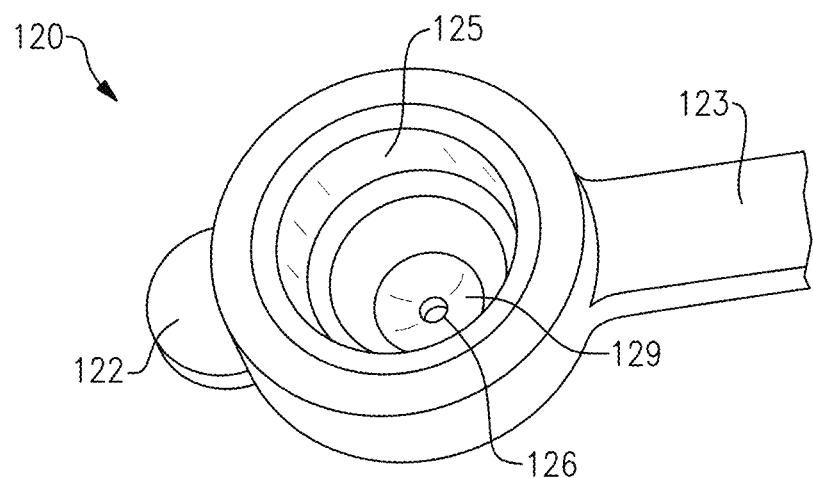
FIG. 3D is a drawing showing an elevated view of the guard cap side of the primary cap of the exemplary biopsy valve of FIG. 3A.
Figure 3E:
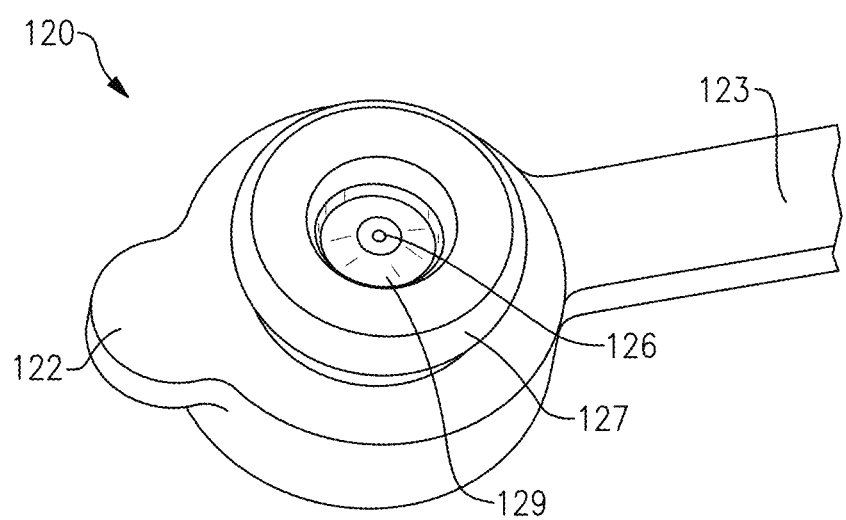
FIG. 3E is a drawing showing an elevated view of the body side of the primary cap of the exemplary biopsy valve of FIG. 3A.
Figure 3F:
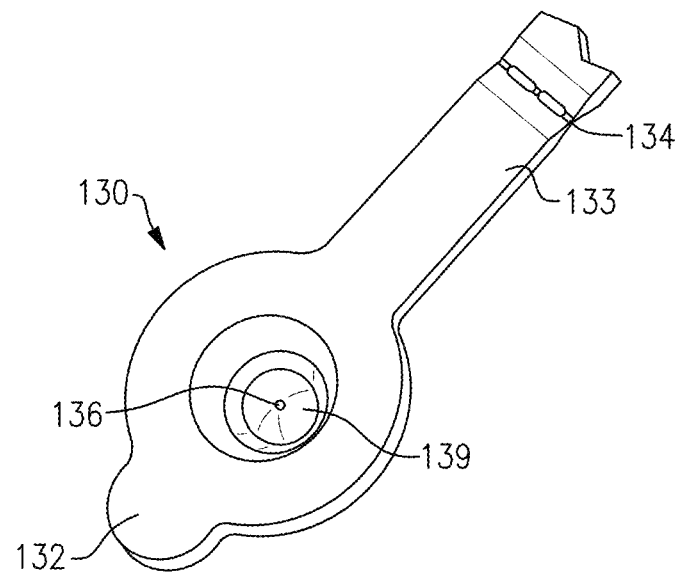
FIG. 3F is a drawing showing an elevated view of the top side of the guard cap of the exemplary biopsy valve of FIG. 3A.
Figure 3G:
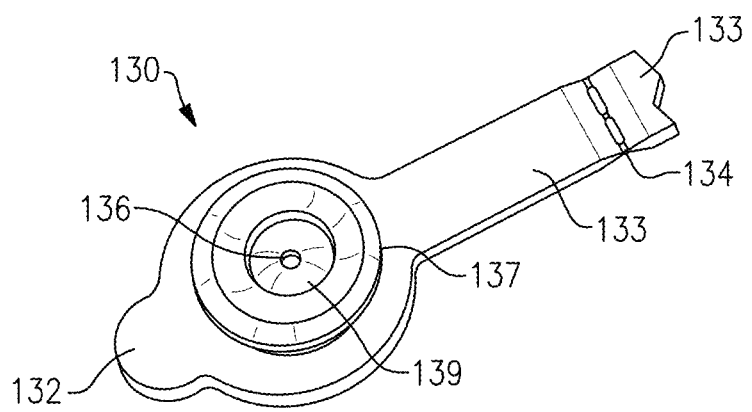
FIG. 3G is a drawing showing an elevated view of the primary cap side of the guard cap of the exemplary biopsy valve of FIG. 3A.
Figure 3I:
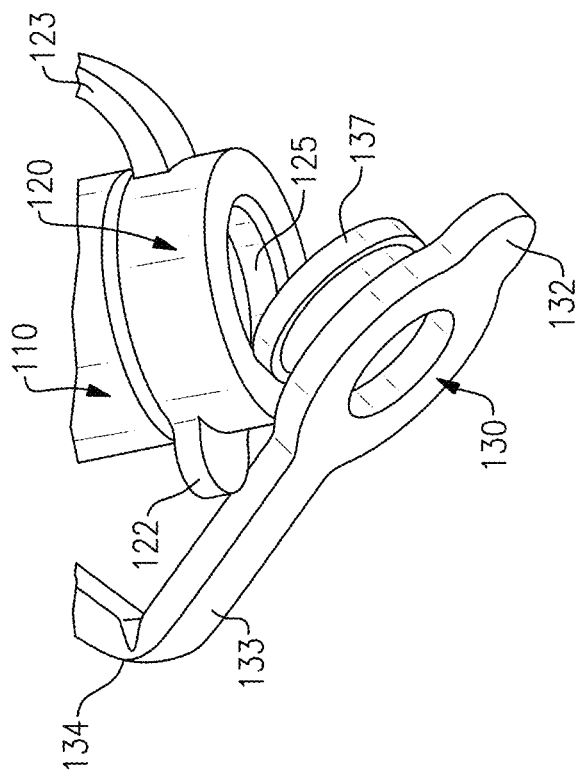
FIG. 3I is a drawing showing an elevated view of the guard cap lip partly inserted into the groove of the primary cap of the exemplary biopsy valve of FIG. 3A.
Figure 3H:
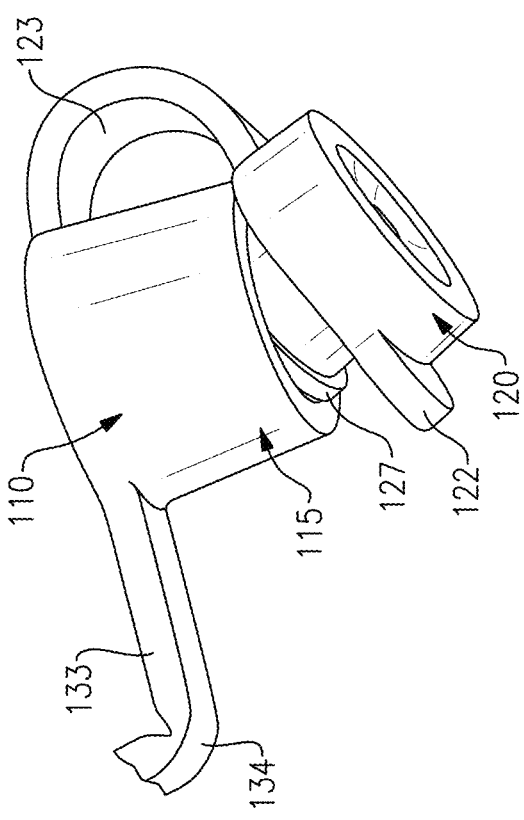
FIG. 3H is a drawing showing a side view of the primary cap lip partly inserted into the body second groove of the exemplary biopsy valve of FIG. 3A.
Figure 3J:
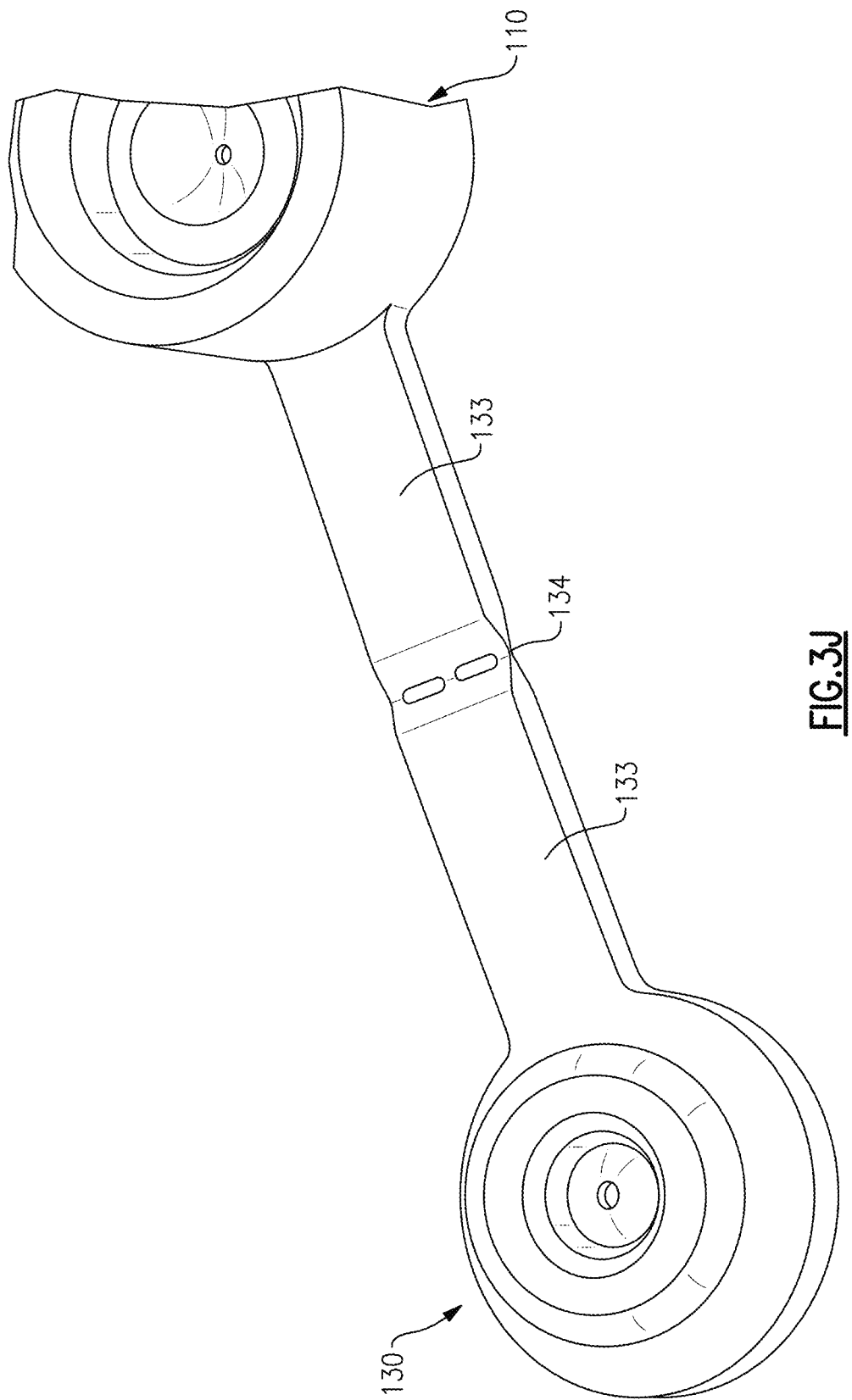
FIG. 3J is a drawing showing an elevated view of a perforated tear line of the guard cap strap of the exemplary biopsy valve of FIG. 3A.

FIG. 3A is a drawing showing a bottom view of an exemplary biopsy valve 100 with accessory tool tactile guard cap position marker according to the Application. FIG. 3B is a drawing showing an elevated view of the primary cap side of the body of the exemplary biopsy valve of FIG. 3A. FIG. 3C is a drawing showing an elevated view of the endoscope working channel side of the body of the exemplary biopsy valve of FIG. 3A. FIG. 3D is a drawing showing an elevated view of the guard cap side of the primary cap of the exemplary biopsy valve of FIG. 3A. FIG. 3E is a drawing showing an elevated view of the body side of the primary cap of the exemplary biopsy valve of FIG. 3A. FIG. 3F is a drawing showing an elevated view of the top side of the guard cap of the exemplary biopsy valve of FIG. 3A. FIG. 3G is a drawing showing an elevated view of the primary cap side of the guard cap of the exemplary biopsy valve of FIG. 3A. FIG. 3H is a drawing showing a side view of the primary cap lip partly inserted into the body second groove of the exemplary biopsy valve of FIG. 3A. FIG. 3I is a drawing showing an elevated view of the guard cap lip partly inserted into the groove of the primary cap of the exemplary biopsy valve of FIG. 3A. FIG. 3J is a drawing showing an elevated view of a perforated tear line of the guard cap strap of the exemplary biopsy valve of FIG. 3A.

With reference to FIG. 3A to FIG. 3J, an exemplary biopsy valve 100 according to the Application includes a body 110 having a first groove 111 adapted to fit over a lip of an endoscope working channel and a second groove 115 and a first membrane 119. A primary cap 120 is mechanically coupled to the body by a primary strap 123 extending between the primary cap 120 and the body 110. The primary cap 120 includes a primary cap lip 127 to couple into the second groove 115 of the body 110, a second membrane 129 and a primary cap groove 125. A guard cap 130 is mechanically coupled to the body 110 by a guard cap strap 133 extending between the guard cap 130 and the body 110. The guard cap 130 includes a guard cap lip 137 which couples into the primary cap groove 125 of the primary cap 110, and a third membrane 139. The guard cap strap 133 can include a perforation and/or tear line to separate the guard cap from the body where the guard cap is used as a tactile position marker. Either or both of the primary cap and the guard cap can include an opening tab 122, 132.

FIG. 4 is a drawing showing a top view of the biopsy valve 100 of FIG. 3A.

Figure 7:
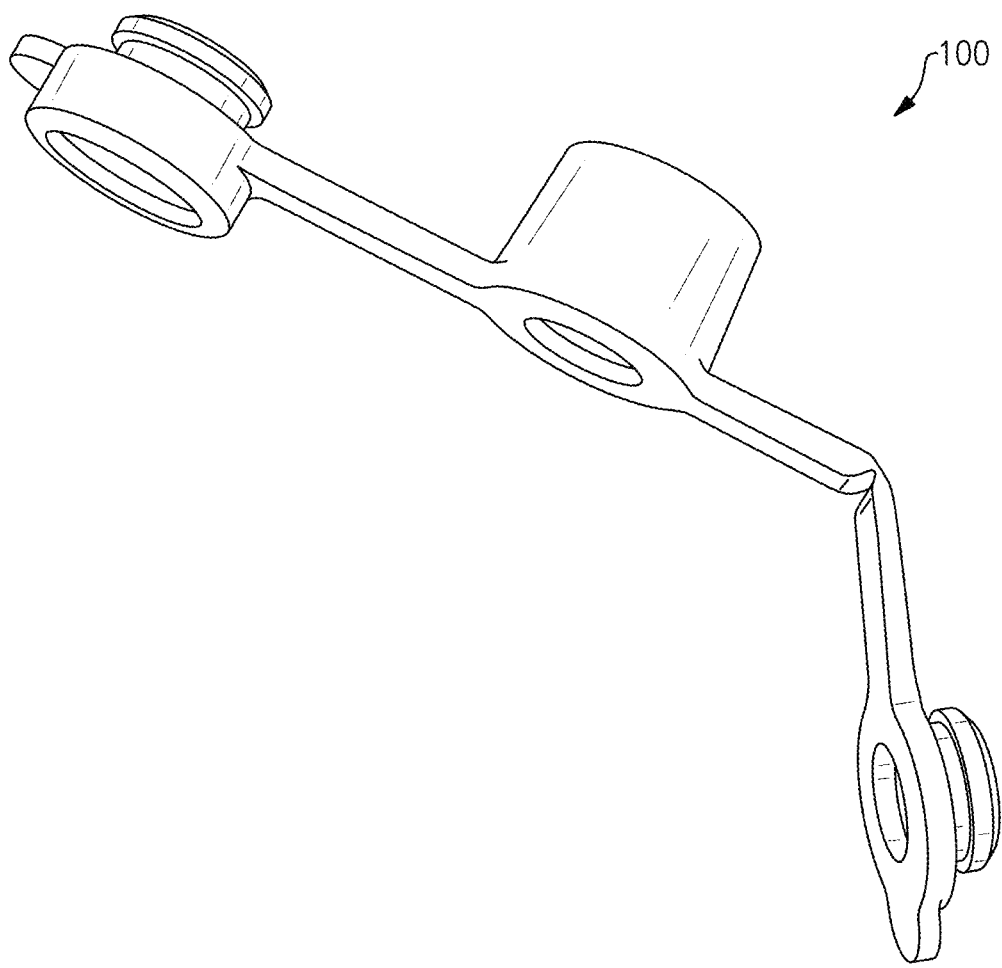
FIG. 7 is a drawing showing an elevated view of the biopsy valve of FIG. 3.

FIG. 5 is a drawing showing a first side view of the biopsy valve 100 of FIG. 3A. FIG. 6 is a drawing showing a second side view of the biopsy valve 100 of FIG. 3A. FIG. 7 is a drawing showing an elevated view of the biopsy valve 100 of FIG. 3A.

Figure 8:
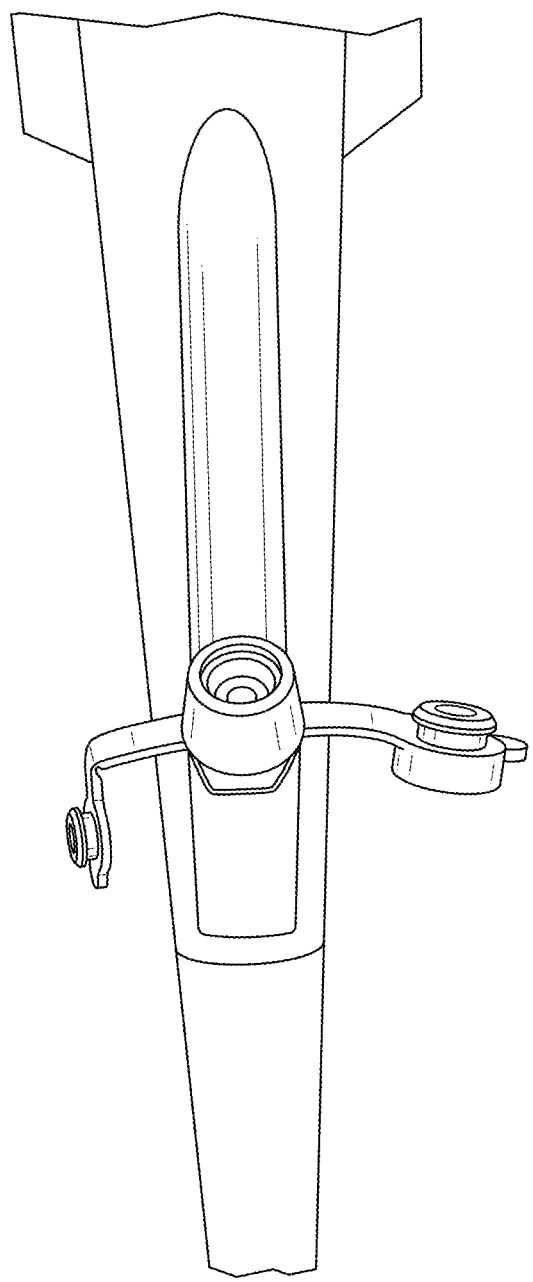
FIG. 8 is a drawing showing the exemplary biopsy valve of FIG. 3A mounted on the apex lip of a working channel of an exemplary endoscope.
Figure 9:
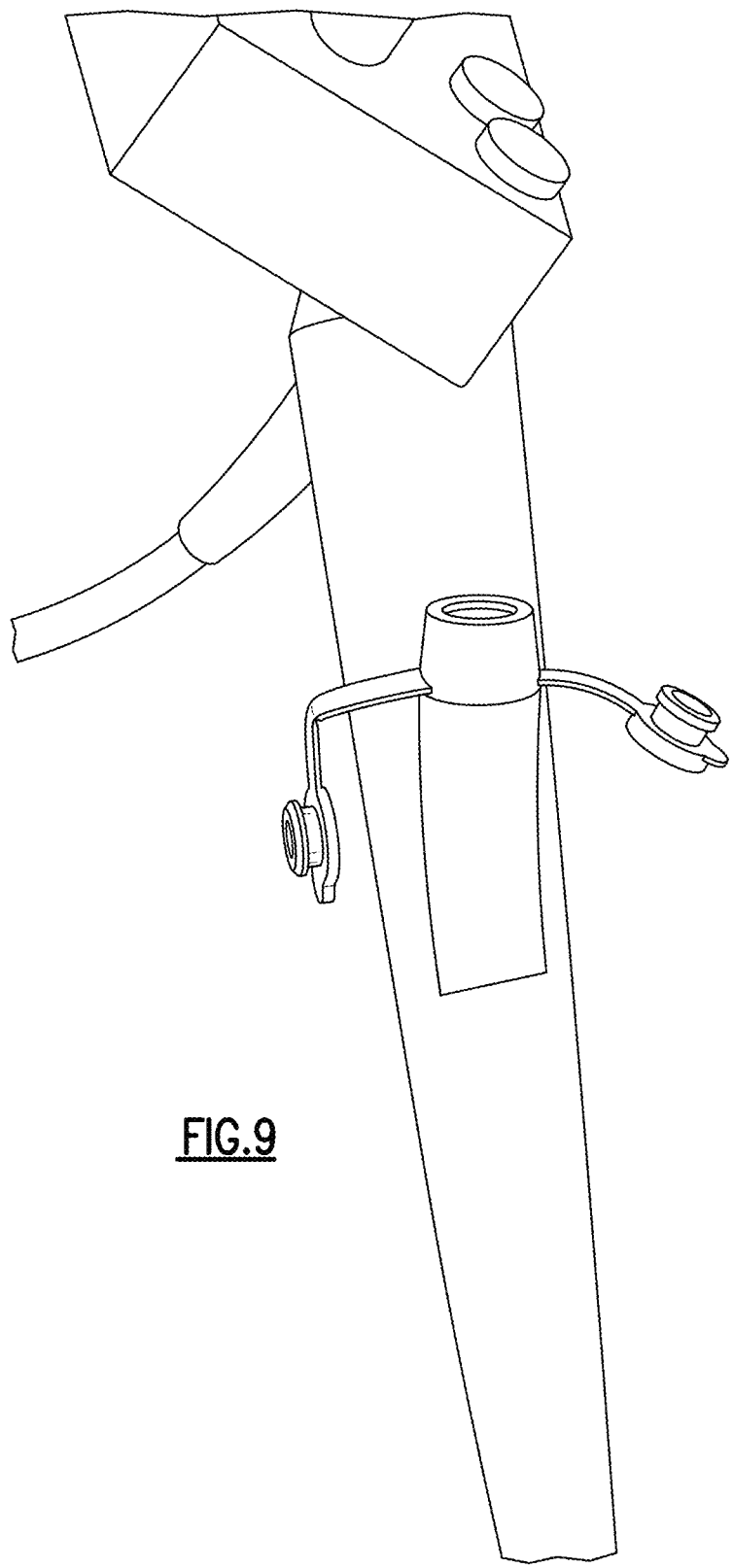
FIG. 9 is a drawing showing another view of the biopsy valve of FIG. 3A mounted on the endoscope.
Figure 10:
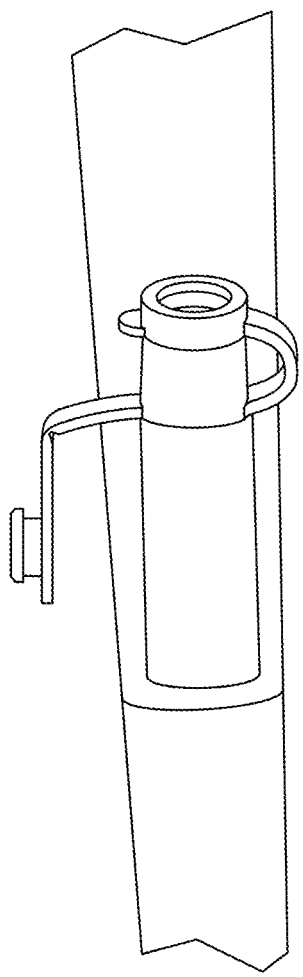
FIG. 10 is a drawing showing the primary cap folded over and plugged into the body of the biopsy valve.

FIG. 8 is a drawing showing the exemplary biopsy valve 100 of FIG. 3A mounted on the apex lip of a working channel of an exemplary endoscope. FIG. 9 is a drawing showing another view of the biopsy valve 100 of FIG. 3A mounted on the endoscope. FIG. 9 is a drawing showing the primary cap 120 folded over and plugged into the body of the biopsy valve. Note that the lip of the primary cap is pushed into a corresponding groove of the top of the biopsy valve body opposite the side of the body of the biopsy valve which is engaged with the lip of the working channel of the endoscope.

Figure 11:
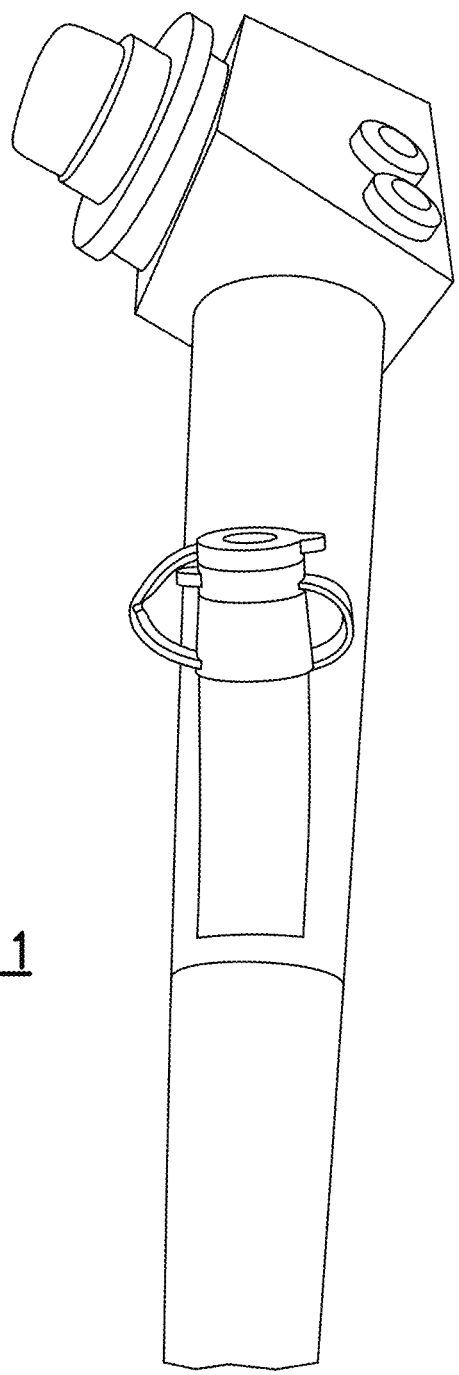
FIG. 11 is a drawing showing the guard cap folded over and pushed into the top of the primary cap.

FIG. 11 is a drawing showing the guard cap 130 folded over and pushed into the top of the primary cap. Note that the lip of the guard cap is pushed into and engaged with the groove at the top of the primary cap opposite to the side of the primary cap which is pushed into and engaged with the body of the biopsy valve. At this stage of installation of the exemplary biopsy valve 100 onto the working channel of the endoscope, there are three successive membranes of protection, sealing, and isolation between the lip of the working channel of the endoscope and the third membrane of the guard cap, through which the shaft of the accessory tool will be inserted into the working channel through the three membranes of the biopsy valve, and further into the insertion tube of the endoscope. The holes or slits in each of the three membranes are of the substantially the same size.

Figure 12:
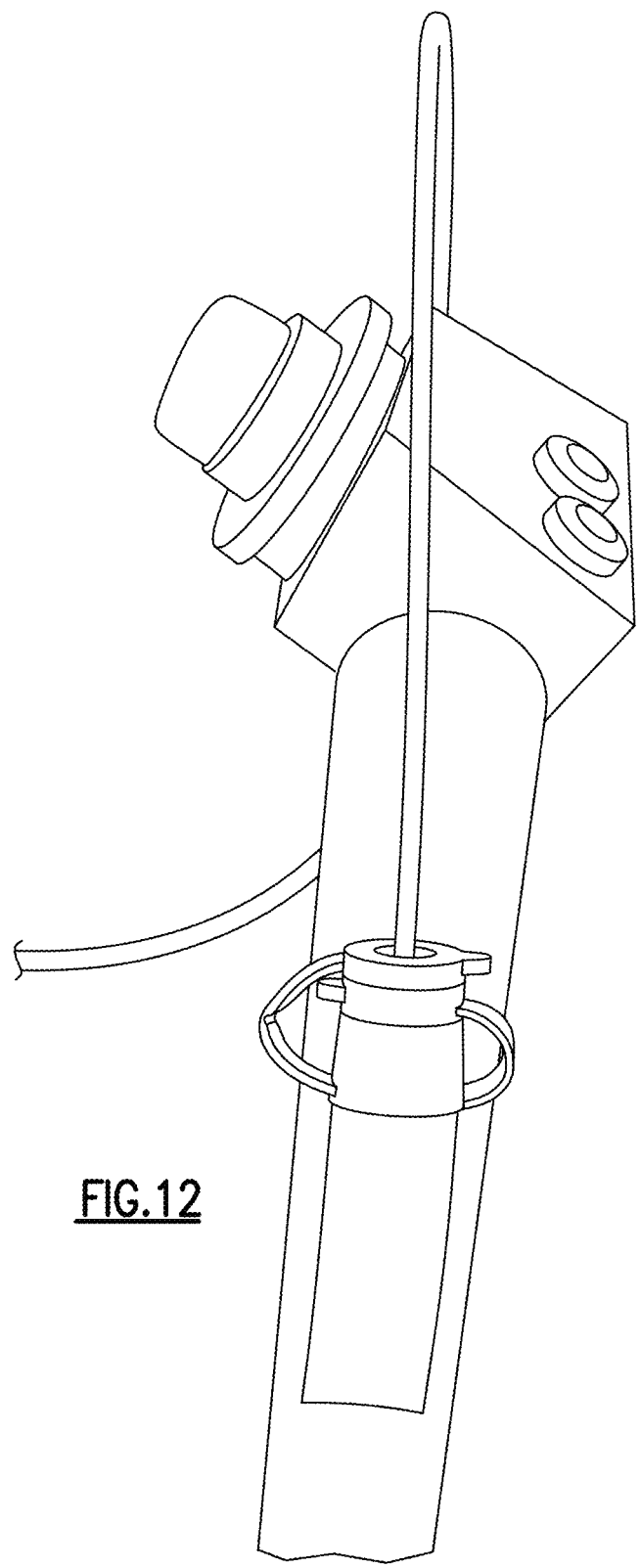
FIG. 12 shows an exemplary shaft of a working tool inserted through the three membranes of the biopsy valve and into the working channel and insertion tube of the endoscope.

FIG. 12 shows an exemplary shaft of a working tool inserted through the three membranes of the biopsy valve 100 and into the working channel and insertion tube of the endoscope.

Figure 13:
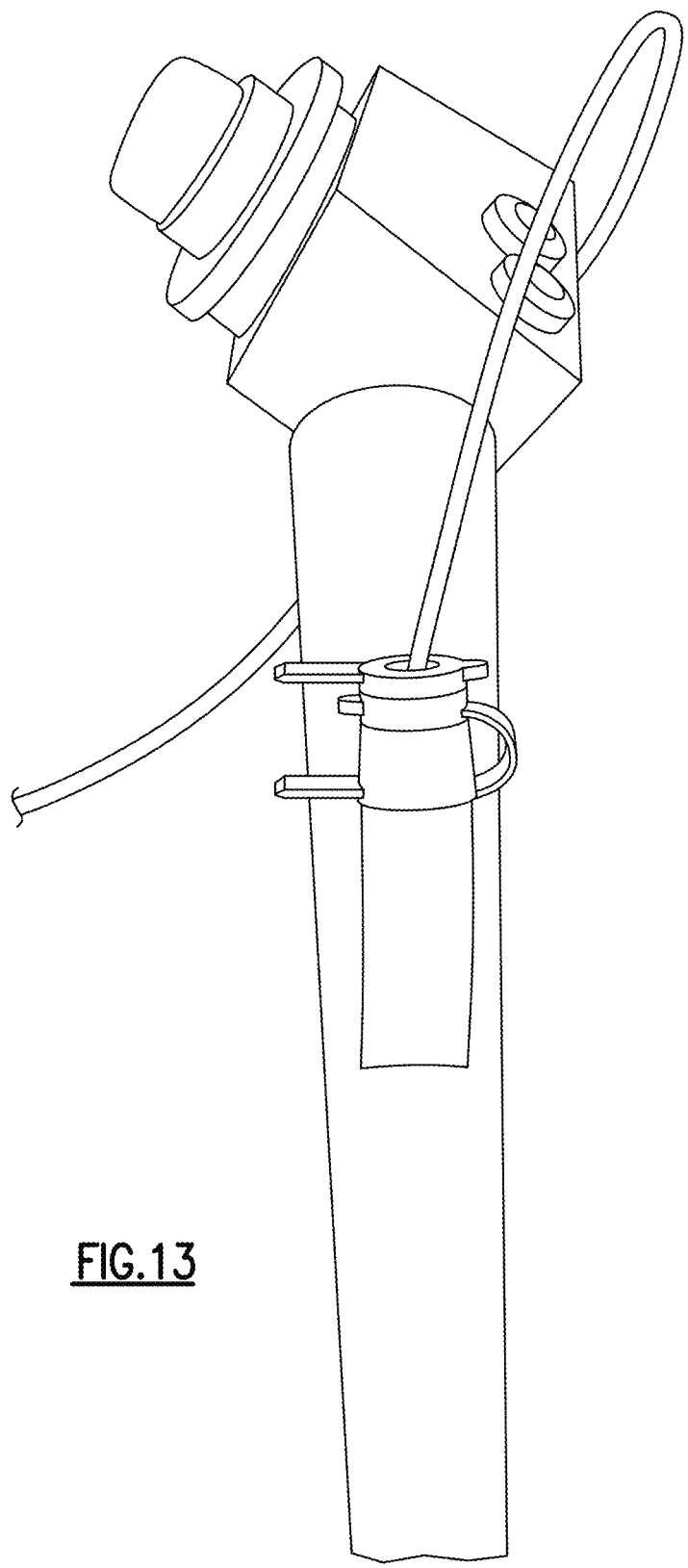
FIG. 13 is a drawing showing the first step of using the exemplary biopsy valve to mark the inserted position of the shaft of the accessory tool using the guard cap.
Figure 14:
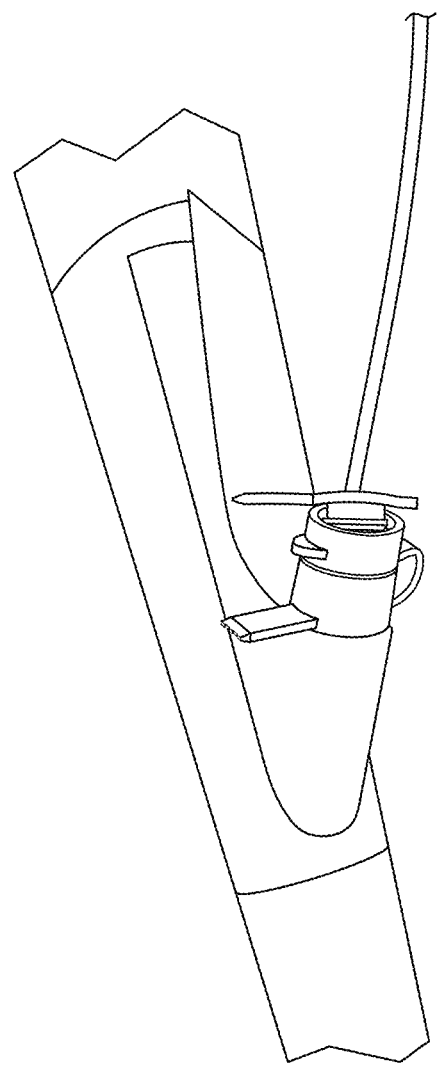
FIG. 14 is drawing showing a severed guard cap strap.

FIG. 13 is a drawing showing the first step of using the exemplary biopsy valve 100 to mark the inserted position of the shaft of the accessory tool using the guard cap. The first step as illustrated by FIG. 13, is to sever the primary strap between said body and said guard cap. FIG. 14 is another view of the severed guard cap strap.

Figure 15B:
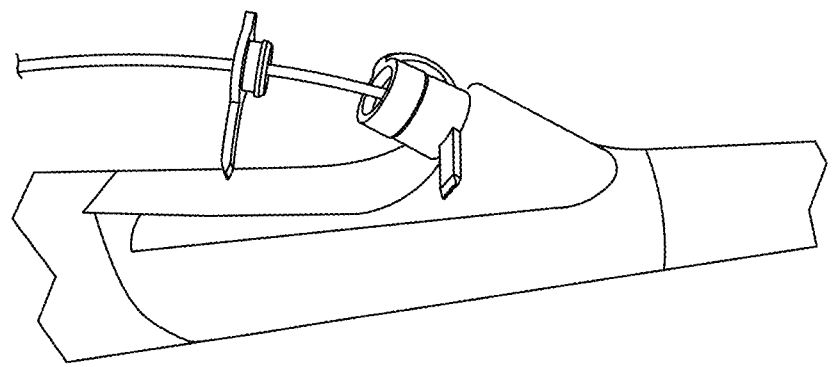
FIG. 15B is a drawing showing the guard cap riding on the shaft of the accessory tool in substantially the same place on the shaft of the accessory tool.
Figure 15A:
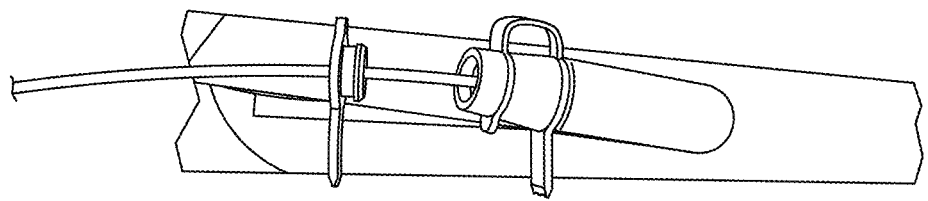
FIG. 15A is a drawing showing the removal of the shaft of the accessory tool from the insertion tube of the endoscope.

FIG. 15A is a drawing showing the removal of the shaft of the accessory tool from the insertion tube of the endoscope, where the guard cap, now unplugged from the top of the primary cap, and affixed by friction via an opening in the guard cap third membrane to the shaft of the accessory tool, rides freely away from the biopsy valve as the shaft of the accessory tool is withdrawn.

FIG. 15B is a drawing showing the guard cap riding on the shaft of the accessory tool in substantially the same place on the shaft of the accessory tool, riding back into the working channel and into the insertion tube of the endoscope. The practitioner reinserting the shaft of the accessory tool feels by tactile feedback when the guard cap comes in contact with the top of the primary cap. On successive withdrawal and reinsertion of the shaft of the accessory tool (e.g. for biopsy tissue removal), the guard cap only touches or comes in contact with the top of the primary cap and need not be plugged into the primary cap. That is, the lip of the guard cap need not be pushed into the groove of the primary cap for successive withdrawals and reinsertions of the shaft of the accessory tool.

Note that while the guard cap can maintain substantially the same position on the shaft of the accessory tool during successive withdrawals and reinsertions of the shaft of the accessory tool by the friction fit between the third membrane of the guard cap and the shaft of the accessory tool. However, the practitioner can still manually adjust the position of the of the guard cap on the shaft of the accessory tool, such as, for example, to make slight position corrections, or when advancing the shaft of the accessory tool to a slightly different position with respect to the end of the insertion tube. However, the location of the working end of the accessory tool is primarily determined by gross position movements of the working end of the insertion tube of the endoscope.

Figure 16B:
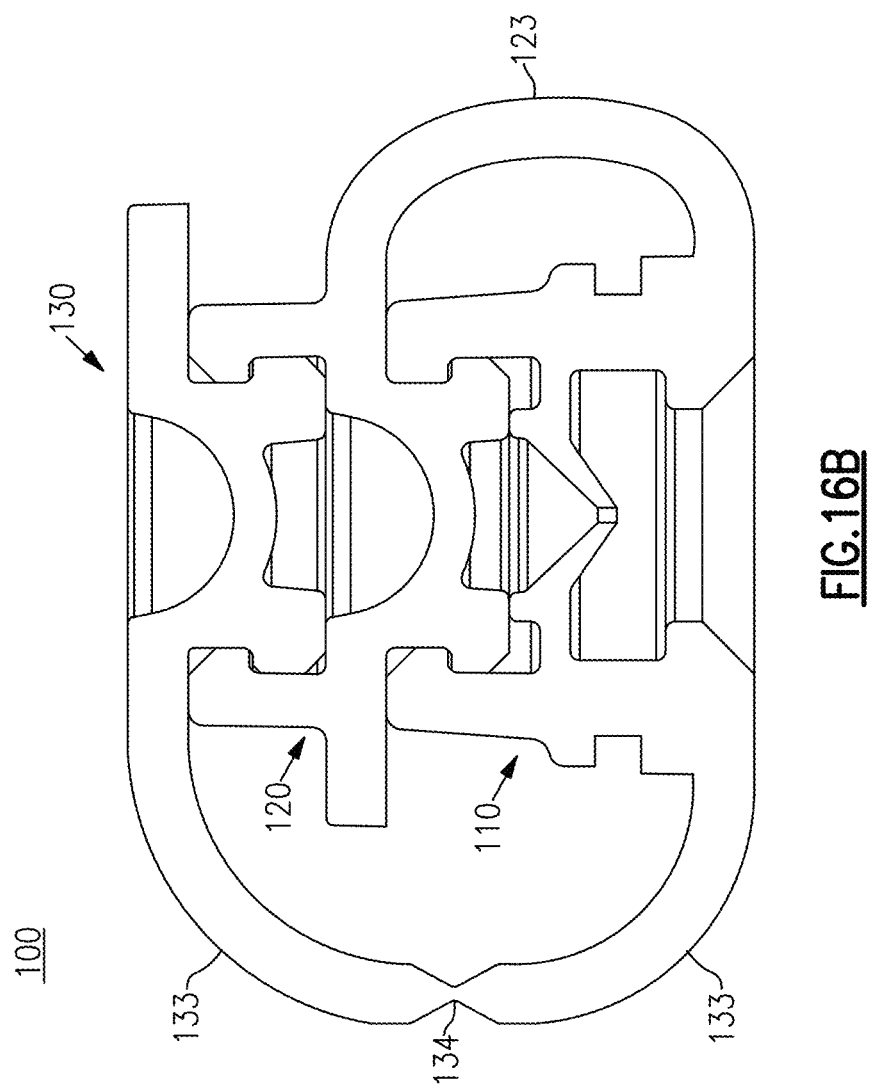
FIG. 16B is a drawing showing a side cut away view of the guard cap affixed to the primary cap, and primary cap affixed the body of the ValveGuard of FIG. 16A.

FIG. 16A is a drawing showing an elevated view of ValveGuard similar to FIG. 4. FIG. 16B is a drawing showing a side cut away view of the guard cap affixed to the primary cap, and primary cap affixed the body of the ValveGuard of FIG. 16A.

In summary, and with reference to the exemplary ValveGuard of FIG. 16A, FIG. 16B, and the similar biopsy valve of FIG. 3A, FIG. 3C, FIG. 3D, a biopsy valve 100 includes a body having a first groove 111 adapted to fit over a lip of an endoscope working channel and a second groove 115 and a first membrane 119. A primary cap 120 is mechanically coupled to the body by a primary strap 123 extending between the primary cap and the body 110. The primary cap 120 includes a primary cap lip 127 to couple into the second groove 115 of the body 110, a second membrane 129 and a primary cap groove 125. A guard cap 130 is mechanically coupled to the body by a guard cap strap 133 extending between the guard cap 130 and the body 110. The guard cap 130 includes a guard cap lip 137 which couples into the primary cap groove 125 of the primary cap 120, and a third membrane 139.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A biopsy valve comprising:
   a body having a first groove adapted to fit over a lip of an endoscope working channel and a second groove and a first membrane;
   a primary cap mechanically coupled to said body by a primary strap extending between said primary cap and said body, said primary cap comprising a primary cap lip to couple into said second groove of said body, a second membrane and a primary cap groove; and
   a guard cap mechanically coupled to said body by a guard cap strap extending between said guard cap and said body, said guard cap comprising a guard cap lip which couples into said primary cap groove of said primary cap, and a third membrane,
   wherein:
      said primary cap is configured to fold over and plug into said body;
      said guard cap is configured to fold over and plug said into said primary cap; and
      said third membrane of said guard cap, said second membrane of said primary cap, and said first membrane of said body are configured to receive a shaft of an accessory tool.

2. The biopsy valve of claim 1, wherein said guard cap strap is longer in length than said primary strap.

3. The biopsy valve of claim 1, wherein said guard cap strap comprises a tear line.

4. The biopsy valve of claim 3, wherein said guard cap is configured to be severed along said tear line and friction fit to a shaft of the accessory tool so as to ride freely on said shaft of the accessory tool when removed from the endoscope working channel, and wherein said guard cap is further configured to touch a top of said primary cap providing a tactile feedback of the shaft of the accessory tool in an insertion tube of the endoscope when said accessory tool is reinserted into the endoscope working channel.

5. The biopsy valve of claim 1, wherein said guard cap strap comprises a perforated tear line.

6. The biopsy valve of claim 1, wherein said biopsy valve comprises a silicone material.

7. The biopsy valve of claim 1, wherein said biopsy valve is a valve manufactured by a molding process.

8. A method of using a biopsy valve with an endoscope working channel comprising:
   providing the biopsy valve with a primary cap and a guard cap;
   installing a body of said biopsy valve onto the endoscope working channel;
   folding over and plugging said primary cap into said body;
   folding over and plugging said guard cap into said primary cap; and
   inserting a shaft of an accessory tool through a third membrane of said guard cap, a second membrane of said primary cap, and a first membrane of said body.

9. The method of claim 8, after said step of inserting, further comprising the step of severing a guard cap strap between said body and said guard cap, and unplugging said guard cap from said primary cap as the shaft of said accessory tool is removed from the working channel, and on reinsertion of the shaft of said accessory tool into the working channel, detecting by a tactile feedback when said guard cap riding by a friction fit at a location on the shaft of said accessory tool touches a top surface of said primary cap.

* * * * *